United States Patent
Lee

(10) Patent No.: US 10,005,854 B2
(45) Date of Patent: Jun. 26, 2018

(54) FUNCTIONALIZED HYDROPHILIC AND LUBRICIOUS POLYMERIC MATRIX AND METHODS OF USING SAME

(75) Inventor: William Lee, Chelsea, MA (US)

(73) Assignee: AST PRODUCTS, INC., Billerica, MA (US)

( * ) Notice: Subject to any disclaimer, the term of this patent is extended or adjusted under 35 U.S.C. 154(b) by 0 days. days.

(21) Appl. No.: 13/320,661

(22) PCT Filed: Sep. 30, 2011

(86) PCT No.: PCT/US2011/054230
§ 371 (c)(1),
(2), (4) Date: Feb. 5, 2013

(87) PCT Pub. No.: WO2012/047755
PCT Pub. Date: Apr. 12, 2012

(65) Prior Publication Data
US 2013/0129953 A1    May 23, 2013

Related U.S. Application Data

(60) Provisional application No. 61/390,212, filed on Oct. 6, 2010.

(51) Int. Cl.
| | |
|---|---|
| *C08F 10/06* | (2006.01) |
| *A61L 29/04* | (2006.01) |
| *A61L 29/06* | (2006.01) |
| *A61L 29/08* | (2006.01) |
| *A61L 29/14* | (2006.01) |
| *C08J 7/18* | (2006.01) |
| *A61L 27/34* | (2006.01) |
| *A61L 27/50* | (2006.01) |

(52) U.S. Cl.
CPC .............. *C08F 10/06* (2013.01); *A61L 27/34* (2013.01); *A61L 27/50* (2013.01); *A61L 29/04* (2013.01); *A61L 29/06* (2013.01); *A61L 29/085* (2013.01); *A61L 29/14* (2013.01); *C08J 7/18* (2013.01); *A61L 2400/10* (2013.01); *A61L 2400/18* (2013.01); *A61L 2430/16* (2013.01); *C08J 2453/00* (2013.01); *Y10T 428/139* (2015.01)

(58) Field of Classification Search
CPC .............................. B01J 20/261; B01J 20/265
See application file for complete search history.

(56) References Cited

U.S. PATENT DOCUMENTS

| | | | | |
|---|---|---|---|---|
| 3,518,176 | A | * | 6/1970 | Russell et al. .................. 522/89 |
| 5,344,455 | A | | 9/1994 | Keogh et al. |
| 5,376,400 | A | * | 12/1994 | Goldberg ................. A61L 27/34 427/2.11 |
| 5,803,925 | A | | 9/1998 | Yang et al. |
| 6,231,876 | B1 | * | 5/2001 | Niessner ................ A61K 8/817 424/401 |
| 2003/0203991 | A1 | | 10/2003 | Thomas et al. |
| 2007/0087113 | A1 | | 4/2007 | Uilk et al. |
| 2009/0169716 | A1 | | 7/2009 | Linhardt et al. |

OTHER PUBLICATIONS

IAEA, 2004, 134 pages.*
International Search Report and Written Opinion, PCT/US2011/054230, dated May 1, 2012 (9 pages).
Lee, et al., "Biocompatible and Autoclavable Hydrophilic Coatings for IOL Inserters" Poster Presentation at Annual Meeting of the Society for Biomaterials (Apr. 14 and 15, 2011), 1 page.

* cited by examiner

*Primary Examiner* — Kyle A Purdy
(74) *Attorney, Agent, or Firm* — John M. Garvey; Hui Zhao; DLA Piper LLP (US)

(57) ABSTRACT

Compositions are provided herein comprising a base polymer having engrafted with a secondary polymeric matrix having hydrophilic and lubricious copolymer brushes. Each copolymer brush further comprises functional groups immobilized along the surface of the brush in a plurality of layers, the functional groups conferring hydrophilic and lubricious properties to the base polymer. These polymer compositions are useful for e.g., fabricating devices for delivery of intraocular lenses (IOLs) as well as improving the hydrophilic properties of contact lenses.

16 Claims, 5 Drawing Sheets

FUNCTIONALIZED HYDROPHILIC AND LUBRICIOUS POLYMERIC MATRIX AND METHODS OF USING SAME

CROSS-REFERENCE TO RELATED APPLICATIONS

This application claims the benefit of PCT/US2011/054230, entitled "Functionalized Hydrophilic and Lubricious Polymeric Matrix and Methods of Using Same," which was filed on Sep. 30, 2011 and U.S. Provisional Patent Application 61/390,212, entitled "Functionalized Hydrophilic and Lubricious Polymeric Matrix and Methods of Using Same," which was filed on Oct. 6, 2010. The entirety of the aforementioned applications is herein incorporated by reference.

FIELD OF THE INVENTION

The present invention relates to medical devices such as contact lenses, intraocular lenses and IOL delivery devices, as well as improved polymers used for the manufacture of such devices.

BACKGROUND OF THE INVENTION

Synthetic polymeric materials are widely used nowadays to fabricate myriads of products, including medical devices. Many of such medical devices, due to its intrinsic surface hydrophobicity, e.g., inserters for intraocular lenses, interventional medical devices or contact lenses, require a hydrophilic and/or lubricious surface.

A number of methods have been developed for applying hydrophilic coatings on polymeric substrates in recent years. However, almost all of the methods involve in physical adsorption of the coating onto the polymeric substrate, or involve in a multiple-step-coating process which is costly and time consuming, or produce a coating that is too thick, especially for an IOL delivery device in that it can cause damage to the IOLs, or produce a coating that cannot withstand steam sterilization, or produce a coating that cannot be stored in a wet state, e.g., water or saline, for a period of years. As a result, there remains a need for a thin, durable and autoclavable hydrophilic and lubricious coating as well as simpler and less expensive coating processes.

Although most of the currently marketed contact lenses are hydrophilic to a large extent, many wearers still experience discomfort, particularly with those contact lenses using silicone as part of the base polymer. Various coating approaches have been made to hydrophilize silicone-based contact lenses but due to the characteristic of the silicone itself, all approaches had failed so far. As a result, there remains a need for improved methods for hydrophilizing contact lenses as well as simpler and less expensive coating processes.

SUMMARY OF THE INVENTION

The present disclosure relates to various engrafted polymer compositions, methods for engrafting a hybrid hydrophilic and lubricious polymeric matrix onto base polymers, and various polymeric medical devices having such engrafted polymer compositions.

An engrafted polymer composition includes a hydrophilic surface, said hydrophilic surface having a secondary engrafted surface matrix of hydrophilic and lubricious copolymers, the engraftment method being described by the steps of: contacting a base polymer with a surface modifying composition having a hydrophilic reactive monomer, a lubricious reactive monomer and a solvent; and initiating radical formation in the base polymer, thereby engrafting the hydrophilic reactive monomers and the lubricious reactive monomers on to the surface of the base polymer.

This method is also useful for modifying a hydrophobic base polymer. A base polymer is obtained that is substantially hydrophobic and a hydrophilic surface is engrafted thereto, said hydrophilic surface having a secondary engrafted surface matrix of hydrophilic and lubricious copolymers, the engraftment method being described by the steps of: contacting the base polymer with a surface modifying composition including a hydrophilic reactive monomer, a lubricious reactive monomer and a solvent; and initiating radical formation in the base polymer;

thereby engrafting the hydrophilic reactive monomers and the lubricious reactive monomers on to the surface of the base polymer thereby providing a hydrophilic surface on the hydrophobic base polymer.

Such engrafted polymers are suitable for fabricating medical devices, such as for example, insertion devices for intraocular lenses, or contact lenses. The base polymers are fabricated according to methods known in the art, and are subjected to the engraftment processes to create engrafted surfaces having a hydrophilic and lubricious copolymer matrix. By way of further example, an inserter for an IOL forms a substantially tubular geometry defining a lumen, where the luminal surface has an engrafted hydrophilic and lubricious copolymer matrix. The IOL delivery is facilitated by the engrafted hydrophilic and lubricious copolymer matrix. For a contact lens, the base polymer forms a substantially concave surface and a substantially convex surface, and the substantially concave surface and substantially convex surface tube both include an engrafted hydrophilic and lubricious copolymer matrix. This increases the wettability and perceived comfort of the contact lens. This is particularly advantageous for hydrophobic materials used in RGP and hard contact lenses.

The method includes (1) contacting the base polymer in a solvent with a combination of two or more surface modifying compositions; (2) sealing the base polymer together with the combination of two or more surface modifying compositions in a liquid barrier container; (3) subjecting the sealed container to a radiant energy source; and (4) washing, rinsing and drying the irradiated polymeric substrate, thereby producing a base polymer bearing an engrafted hydrophilic and lubricious secondary polymeric matrix on its surface.

More specifically, the base polymer is engrafted with hydrophilic and lubricious copolymer brushes due to the two or more surface modifying compositions. Each copolymer brush further comprises two or more functional groups immobilized along the surface of the brush in a plurality of layers, which confer hydrophilic and lubricious properties to the base polymer compositions.

Moldable polymeric material that can be used to prepare the base polymer include but are not limited to polypropylene, polycarbonate, polyethylene, acryl-butadienestyrene, polyamide, polychlorotrifluoroethylene, polytetrafluoroethylene, polyvinyl chloride, polyvinylidene fluoride, polyvinylchloride, polydimethylsiloxane, polyethylene terephthalate, ethylene tetrafluoroethylene, ethylene chlorotrifluoroethylene, perfluoroalkoxy, styrene, polymethylpentene, polymethylmethacrylate, polystyrene, polyetheretherketone, tetrafluoroethylene, polyurethane, poly(methyl methacrylate), poly(2-hydroxyethyl methacrylate), nylon, polyether block amide and silicone. Among them, polypropylene and polycarbonate are preferred for intraocular lens inserters; and poly(methyl methacrylate), poly(2-hydroxyethyl methacrylate) and silicone are preferred for contact lenses.

Suitable surface modifying compositions or reactive monomers for use in this method, refers to compounds that are capable of participating in a graft polymerization reaction, to be engrafted and polymerized to form hydrophilic and lubricious copolymer brushes include but are not limited to the combination of two or more vinyl monomers or heterocyclic monomers or both, such as 2-acrylamido-2-methylpropane sulfonic acid, 2-hydroxyethyl methacrylate, and Nvinylpyrrolidone. Other specific examples of suitable reactive monomers include vinyl monomers containing a glycidyl group, e.g., glycidyl methacrylate, glycidyl acrylate, glycidyl methylitaconate, ethyl glycidyl maleate, and glycidyl vinyl sulfonate; and vinyl monomers containing a cyano group, e.g., acrylonitrile, vinylidene cyanide, crotononitrile, methacrylonitrile, chloroacrylonitrile, 2-cyanoethyl methacrylate, and 2-cyanoethyl acrylate. Reactive monomers that have hydrophilic groups and that are useful in the present invention include, for example, vinylbenzyl-trimethyl ammonium salt, diethylaminoethyl methacrylate, dimethylaminoethyl acrylate, dimethylaminoethyl methacrylate, diethylaminoethyl acrylate, diethylaminomethyl methacrylate, tertiary-butylaminoethyl acrylate, tertiary-butylaminoethyl methacrylate and dimethylaminopropylacrylamide, acrylic acid, methacrylic acid, styrenesulfonic acid and salts thereof, hydroxyethyl methacrylate, hydroxypropyl acrylate, vinyl pyrrolidone, dimethylacrylamide, ethylene glycol monomethacrylate, ethylene glycol monoacrylate, ethylene glycol dimethacrylate, ethylene glycol diacrylate, triethylene glycol diacrylate and triethylene glycol methacrylate.

Suitable organic solvents for use in this method include but are not limited to various alcohols, dimethyl sulfoxide and N,N-dimethylformamide.

Suitable radiant energy source for graft copolymerization include but are not limited to alpha rays, beta rays, gamma rays, accelerated electron rays, X-rays, or ultraviolet rays. Copolymerization induced by gamma rays or accelerated electron rays provides a convenient radiation source for the graft copolymerization method.

Another aspect of this invention is a base polymer having an engrafted secondary hydrophilic and lubricious polymeric matrix prepared by the above-described method. Thus, also within the scope of this invention is a polymeric composite including a base polymer formed of a moldable polymer and an engrafted secondary polymeric matrix containing hydrophilic and lubricious copolymer brushes by copolymerized onto the base polymer.

One embodiment of the above-described polymeric composite can be a fabricated medical device, e.g., a part of a device for receiving and delivering an intraocular lens into an eye. More specifically, such an exemplary device includes a tapered tube formed of a moldable base polymer and a secondary polymeric matrix containing hydrophilic and lubricious copolymer brushes by copolymerization onto the base polymer. Given the hydrophilic and lubricious inner surface of the tube, an intraocular lens placed in it can be easily folded and pushed therethrough by a plunger configured to enter the tube from the wide end, pushing the IOL through the tapered end of the delivery tube into the eye without damage to the IOL. Moreover, the above-described polymeric composite is suitable for steam sterilization, while sustaining its hydrophilicity and lubricity as well as its intraocular lens delivery performance.

Another embodiment of the above-described polymeric composite can be part of a contact lens. More specifically, the contact lens formed of a moldable base polymer and a secondary polymeric matrix containing hydrophilic and lubricious copolymer brushes by copolymerization onto the surface of the contact lens. Given the hydrophilic and lubricious surface of the contact lens, it provides improved comfort for the wearers.

The hydrophilic and lubricious surface modification method of this invention is simple, durable, inexpensive, and reliable, as it is based on an unexpected finding that a durable and autoclavable hybrid hydrophilic and lubricous copolymer brush that can be engrafted onto a base polymer. Other features or advantages of the present invention will be apparent from the following detailed description of several embodiments, and also from the appending claims.

DETAILED DESCRIPTION OF THE INVENTION

Figure 1:
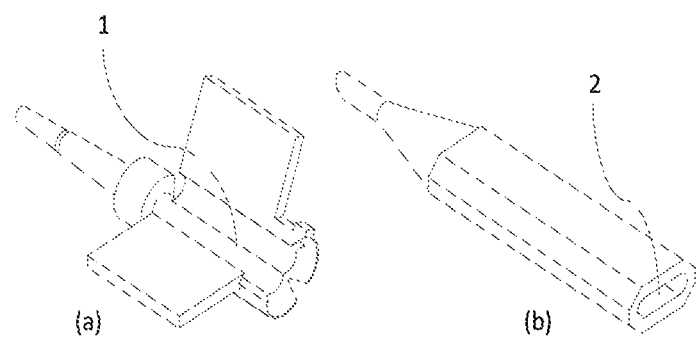
FIG. 1 shows two generic inserters for loading intraocular lenses: (a) generic butterfly-type IOL inserter and (b) a generic closed-type IOL inserter. Intraocular lenses are loaded onto area 1 or into area 2 when in use. Areas where the intraocular lens will travel are modified by engrafting with layered hydrophilic and lubricious polymer brushes. The generic closed-type IOL inserter can also be made into a preloaded IOL delivery system where the IOL will sit in the loading area.
Figure 2:
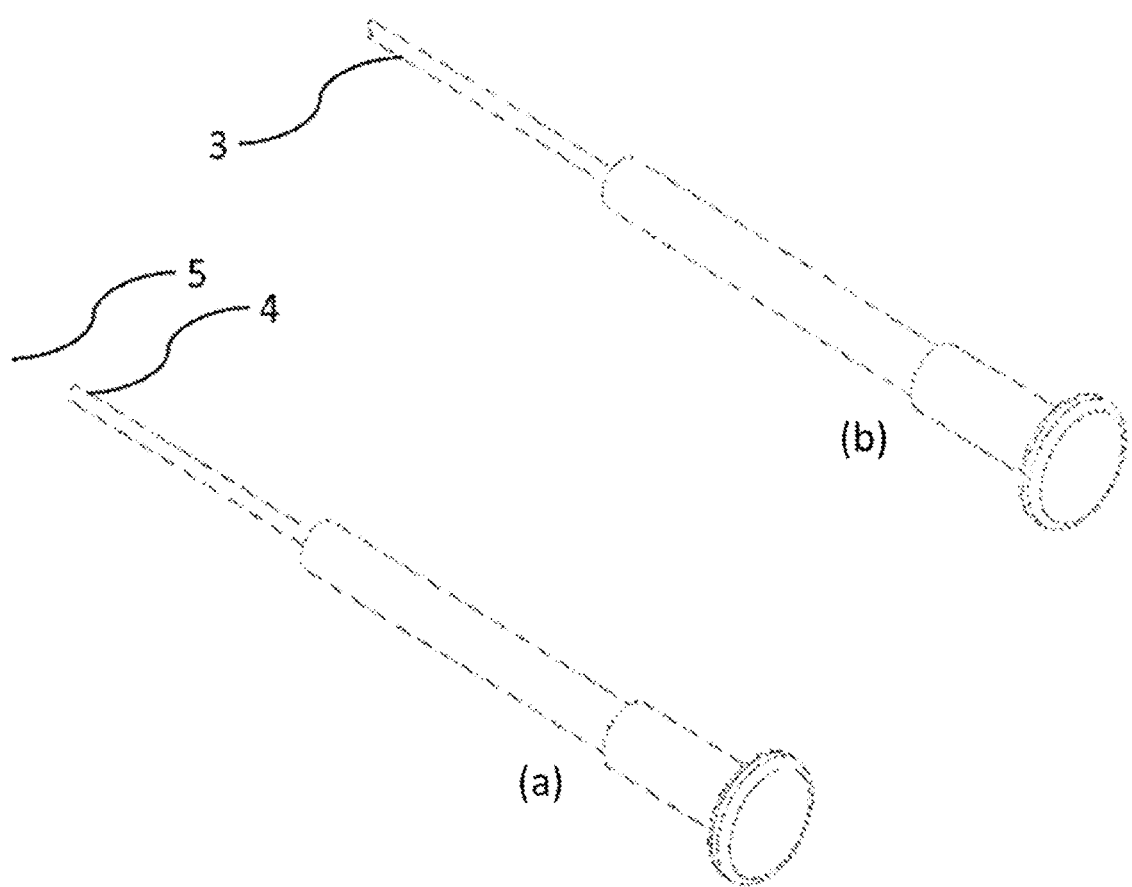
FIG. 2 shows two different needles of the intraocular lens plunger for pushing intraocular lens through the inserters in FIG. 1, (a) the needle 4 with a silicone tip 5 for pushing one-piece intraocular lens and (b) the open-mouth-type needle 3 at the distal end for pushing three-piece intraocular lens. The silicone tip 5 can also be modified by engrafting with hydrophilic and lubricious groups to ease the friction from pushing the intraocular lens and its travel through the inserter tube.
Figure 3:
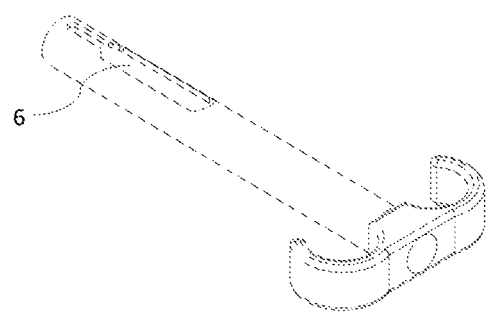
FIG. 3 shows the housing of the needles from FIG. 2 and the area 6 where the inserter from FIG. 1 is to be inserted. The inner wall of the housing can be modified by engrafting hydrophilic and lubricious groups to ease the travel of the needle with or without the silicone tip 5.
Figure 4:
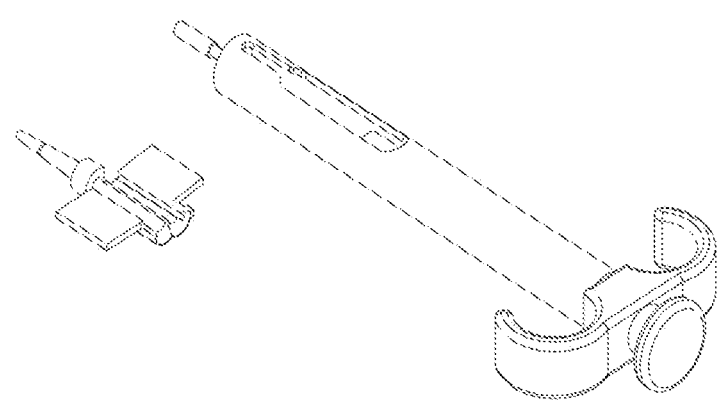
FIG. 4 shows the needle 4 with a silicone tip 5 inside the housing and the generic butterfly-type inserter on the side for delivering one-piece intraocular lens. All components can be configured together to form a preloaded IOL delivery system to ease the loading/insertion of intraocular lens.
Figure 5:
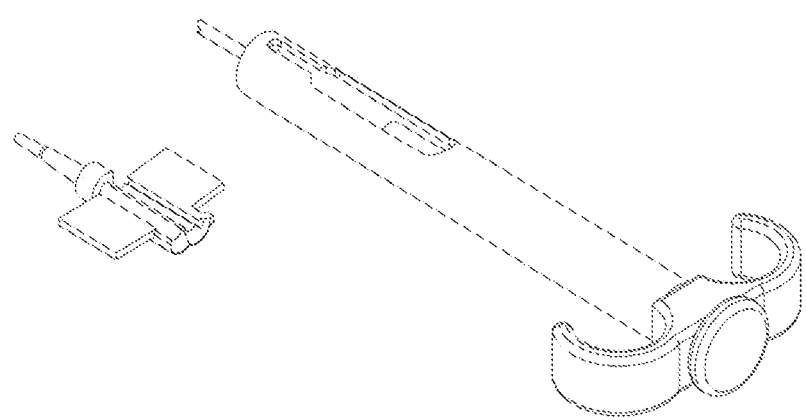
FIG. 5 shows the open-mouth-type needle 3 inside the housing and the generic butterfly-type inserter on the side for delivering three-piece intraocular lens. All components can be configured together to form a preloaded IOL delivery system to ease the loading/insertion of intraocular lens.

The present disclosure details polymer compositions having engrafted hydrophilic and lubricious groups. Also disclosed are such engrafting methods, as well as exemplary polymeric medical devices that advantageously employ such hydrophilic and lubricious polymers in their construction.

Polypropylene and polycarbonate are preferred moldable base polymers for forming substrates for use in the present invention, for delivering intraocular lenses in view of their low cost, inert property, and well-studied behavior in molding and processing. Many other polymers, such as polyamide, cellulose acetate, and acrylic polymer or copolymer are also suitable base polymers for engrafting, and can also be molded into appropriate forms for device manufacture.

Silicone, poly(methyl methacrylate) and poly (2-hydroxyethyl methacrylate) are preferred moldable base polymers for use in the present invention as contact lenses in view of their low cost, inert property, and well-studied behavior in molding and processing. Many other polymers or copolymers, such as polytetrafluoroethylene, and acrylic polymer or copolymer, are also suitable.

To practice the method of this invention, a polymer substrate is immersed and sealed in a liquid barrier container having one or a combination of two or more surface modifying reactive monomers, prior to subjecting the container and the enclosed polymer, to a radiant energy source for initiating the graft-copolymerization reaction.

Graft copolymerization can be carried out, for example, by copolymerization in the presence of a chemical or inducible polymerization initiator, thermal polymerization, irradiation-induced polymerization using ionizing radiation (e.g., alpha rays, beta rays, gamma rays, accelerated electron rays. X-rays, or ultraviolet rays). Copolymerization induced by gamma rays or accelerated electron rays provides a convenient graft copolymerization method.

Several methods of graft copolymerization of reactive vinyl monomers to a base polymer exist. The base polymer can be an already formed article or it can be manufactured into a product or device at a later time. Liquid phase copolymerization, in which a formed article is directly reacted with liquid reactive monomers, and gaseous or vapor phase polymerization, in which a formed article is brought into contact with vapors or gases of reactive monomers, are two copolymerization methods that are useful in the present invention according to the end use or purpose.

Graft copolymerization of the reactive vinyl monomers to the base polymer using a radiant energy source is performed via three different ways: (a) pre-irradiation; (b) peroxidation and (c) mutual irradiation technique. In the pre-irradiation graft copolymerization technique, the base polymer backbone is irradiated in vacuum or in the presence of an inert gas to form radicals. The irradiated base polymer is then treated with vinyl monomers, which is either liquid or vapor or as a solution in a suitable solvent. However, in the peroxidation graft copolymerization method, the base polymer is subjected to high-energy radiation in the presence of air or oxygen. The result is the formation of hydroperoxides or diperoxides depending on the nature of the polymeric backbone and the irradiation conditions. The peroxy products, which are stable, are then treated with vinyl monomers at higher temperature, whence the peroxides undergo decomposition to radicals, which then initiate graft copolymerization. The advantage of this technique is that the intermediate peroxy products can be stored for long periods before performing the graft copolymerization step. On the other hand, with the mutual irradiation graft copolymerization technique, the base polymer and vinyl monomers are irradiated simultaneously to form the radicals and thus addition takes place. The mutual irradiation graft copolymerization technique is useful and cost-effective in the present invention according to the end use or purpose.

The base polymer surfaces activated in this way are graft copolymerized in a solution comprising reactive vinyl monomers. A reactive vinyl monomer is any compound that is capable of participating in a radical induced graft polymerization reaction. The reactive vinyl monomer thus incorporates in the side chain reaction, and forms a polymer brush. The term monomer is used for simplicity, as side reactions between reactive monomers can create oligomers before these are in turn involved in the polymerization reaction with the base polymer, and oligomers or even polymers are also useful reactive species for the present invention. One, two, three, or more different reactive vinyl monomers can be graft-copolymerized to the base polymer in such a manner. As described above, side chain brushes formed by two or more vinyl monomers can be obtained, comprising multiple functional groups, i.e., two or more functional groups on a single polymer brush.

The base polymer and reactive vinyl monomer may be the same compound, for example, a polyethylene base material may utilize ethylene monomers or polymers in the graft polymerization reaction. Reactive vinyl monomers that can be used in the present invention include, for example, vinyl monomers and heterocyclic monomers. Other specific examples of suitable reactive monomers include vinyl monomers containing a glycidyl group, e.g., glycidyl methacrylate, glycidyl acrylate, glycidyl methylitaconate, ethyl glycidyl maleate, and glycidyl vinyl sulfonate; and vinyl monomers containing a cyano group, e.g., acrylonitrile, vinylidene cyanide, crotononitrile, methacrylonitrile, chloroacrylonitrile, 2-cyanoethyl methacrylate, and 2-cyanoethyl acrylate; and vinyl monomers containing an acidic or a basic group, e.g., acrylic acid, methacrylic acid, styrenesulfonic acid and salts thereof, and 2-acrylamido-2methylpropanesulfonic acid; or vinylbenzyltrimethyl ammonium salt, diethylaminoethyl methacrylate, dimethylaminoethyl acrylate, dimethylaminoethyl methacrylate, diethylaminoethyl acrylate, diethylaminomethyl methacrylate, tertiarybutylaminoethyl acrylate, tertiarybutylaminoethyl methacrylate and dimethylaminopropylacrylamide.

Two or more kinds of hydrophilic substances can be copolymerized onto the same polymer brush. Such hydrophilic groups are capable of trapping the water molecules present in air, forming a layer of adsorbed water on the surface of the base polymer of the present invention.

The formed hydrophilic copolymer brushes swell in the presence of water to provide a hydrophilic and lubricious surface.

Thus, the resulting base polymer comprises a plurality of engrafted copolymer brushes which further comprise functional groups attached thereto. These compositions provide a wide range of combinations, and are useful in diverse processes, for example, the products and processes disclosed herein, as well as similar applications known to those of skill in the environmental, separation and filtration, medical, pharmaceutical and biotechnology arts. Such equivalent compositions and processes are considered to be within the scope of the invention. The durability of the hydrophilic and lubricious polymeric matrix can be qualitatively determined by retention of the slippery feel when wet or when rubbed. Other durability tests include, but are not limited to, a measurement of lubricity retained after steam sterilization and multi-measurements of friction. In testing of coated intraocular lens inserters, the presence of more coating residue on the delivered lens is indicative of poorer durability of the hydrophilic polymer layer. The graft copolymerized intraocular lens inserters in the present invention are autoclavable, thin and free from any coating residue that can be transferred onto the intraocular lens during the intraocular lens delivery process.

The invention will be further described in the following examples, which do not limit the scope of the invention described in the claims.

EXAMPLES

Example 1

Mutual Irradiation Graft Copolymerization of Hydrophilic and Lubricious Copolymer Brushes onto Polypropylene-Based IOL Inserters.

Typical butterfly-type polypropylene (PP)-based IOL inserters were used as the base polymer. 2-hydroxyethyl methacrylate (HEMA) was used as the hydrophilic reactive monomer and 2acrylamido-2-methylpropane sulfonic acid (AMPS) was used as the lubricious reactive monomer. The mixtures of HEMA and AMPS at various molar ratios were prepared as shown in Table 1. In all mixtures, two different types of solvent, e.g., butanol and isopropyl alcohol, were used.

A graft copolymerization scheme of the PP-based inserters containing hydrophilic and lubricious copolymer brushes consists of three steps: (1) contacting the PP-based inserter with a mixture of two reactive vinyl monomers, e.g., 2-hydroxyethyl methacrylate (HEMA) and 2acrylamido-2-methylpropane sulfonic acid (AMPS) in a solvent, e.g., isopropyl alcohol or butanol; (2) sealing the PP-based inserter together with the mixture of HEMA and AMPS in a liquid barrier container; (3) subjecting the sealed container to electron-beam irradiation at a total exposed dose from 10 to 200 kGy; (4) washing, rinsing and drying the graft copolymerized PP-based inserter, thereby producing a polymeric composite with a thin, durable and autoclavable hydrophilic and lubricious secondary polymeric matrix. Resultant hydrophilic and lubricious polymer compositions of various preparation conditions were subjected to intraocular lens (IOL) delivery tests before and after steam sterilization, and their results are shown in Table 2. PP based IOL inserters were obtained with excellent hydrophilicity and lubricity. All IOLs delivered by such graft copolymerized inserters were without damage. And there was no coating from luminal surface of the inserter been transferred onto the surface of the IOLs. Moreover, unlike commercially available IOL inserters, such inserters can be steam-sterilized without any damage to the hydrophilic and lubricious polymeric matrix.

TABLE 1

| Solution # | AMPS:HEMA Molar Ratio | Solvent |
| --- | --- | --- |
| 1 | 1:1 | Butanol |
| 2 | 1:1 | IPA |
| 3 | 1:0.8 | Butanol |
| 4 | 1:0.8 | IPA |
| 5 | 1:0.7 | Butanol |
| 6 | 1:0.7 | IPA |
| 7 | 1:0.6 | Butanol |
| 8 | 1:0.6 | IPA |
| 9 | 1:1 | Butanol |
| 10 | 1:1 | IPA |
| 11 | 1:0.8 | Butanol |
| 12 | 1:0.8 | IPA |
| 13 | 1:0.7 | Butanol |
| 14 | 1:0.7 | IPA |
| 15 | 1:0.6 | Butanol |
| 16 | 1:0.6 | IPA |

TABLE 2

| Sample # | Solution # | Dose [kGy] | Lens delivery test before autoclave | Lens delivery test after autoclave |
| --- | --- | --- | --- | --- |
| 1 | 1 | 25 | ••••• | ••••• |
| 2 |   | 50 | •••• | •••• |
| 3 |   | 100 | •••• | ••• |
| 4 |   | 200 | •••• | •••• |
| 5 | 2 | 25 | •••• | ••• |
| 6 |   | 50 | •••• | ••• |
| 7 |   | 100 | •••• | ••• |
| 8 |   | 200 | ••• | • |
| 9 | 3 | 25 | ••••• | ••••• |
| 10 |   | 50 | •••• | •••• |
| 11 |   | 100 | •••• | •••• |
| 12 |   | 200 | •••• | •••• |
| 13 | 4 | 25 | •••• | •••• |
| 14 |   | 50 | • | N/A |
| 15 |   | 100 | ••• | •• |
| 16 |   | 200 | • | N/A |
| 17 | 5 | 25 | ••••• | ••••• |
| 18 |   | 50 | •••• | •••• |
| 19 |   | 100 | •• | N/A |
| 20 |   | 200 | ••• | •••• |
| 21 | 6 | 25 | • | N/A |
| 22 |   | 50 | ••• | •••• |
| 23 |   | 100 | ••• | ••• |
| 24 |   | 200 | •• | N/A |
| 25 | 7 | 25 | •••• | ••••• |
| 26 |   | 50 | •••• | ••••• |
| 27 |   | 100 | ••• | ••••• |
| 28 |   | 200 | ••• | •••• |
| 33 | 9 | 25 | •••• | ••••• |
| 34 |   | 50 | •••• | •••• |
| 35 |   | 100 | •••• | •••• |
| 36 |   | 200 | ••• | •••• |
| 37 | 10 | 25 | •• | N/A |
| 38 |   | 50 | •••• | •••• |
| 39 |   | 100 | ••• | ••• |
| 40 |   | 200 | • | N/A |
| 41 | 11 | 25 | •••• | ••••• |
| 42 |   | 50 | •••• | ••••• |
| 43 |   | 100 | •••• | ••••• |
| 44 |   | 200 | ••• | ••• |
| 49 | 13 | 25 | •••• | ••••• |
| 50 |   | 50 | •••• | ••••• |
| 51 |   | 100 | •••• | ••••• |
| 52 |   | 200 | •••• | •••• |
| 57 | 15 | 25 | •••• | ••••• |
| 58 |   | 50 | •••• | ••••• |
| 59 |   | 100 | •••• | ••••• |
| 60 |   | 200 | ••• | •••• |

••••• Excellent lubricity
•••• Good lubricity
••• Medium lubricity. Slight force needed for lens delivery
•• Lens stuck in the nozzle
• Lens delivery failed

Example 2

Mutual Irradiation Graft Copolymerization of Hydrophilic and Lubricious Copolymer Brushes onto Polypropylene-Based IOL Inserters.

Typical butterfly-type polypropylene (PP)-based IOL inserters were used as the base polymer. 2-hydroxyethyl methacrylate (HEMA) was used as the hydrophilic reactive monomer and acrylic acid (AA) was used as the lubricious reactive monomer. The molar ratio of HEMA:AA was set at 1:1. The electron-beam irradiation dose was set at 25 kGy. All experimental methods followed Example 1. The resultant hydrophilic and lubricious polymer compositions were subjected to intraocular lens (IOL) delivery tests before and after steam sterilization, and their results showed excellent hydrophilicity and lubricity. All IOLs delivered by such graft copolymerized inserters were without damage. And there was no coating from luminal surface of the inserter been transferred onto the surface of the IOLs. Moreover, unlike commercially available IOL inserters, such inserters can be steam-sterilized without any damage to the hydrophilic and lubricious polymeric matrix.

Example 3

Ageing Tests for the Hydrophilic and Lubricious IOL Inserters.

All hydrophilic and lubricious IOL inserters from Example 1 and Example 2 were subjected to (a) 2-year accelerated ageing test at 60° C. and (b) 1-year storage in water. After each specific time, intraocular lens delivery tests were performed. The results had shown equal excellent hydrophilicity and lubricity to those of before and after autoclave. All IOLs delivered by such graft copolymerized inserters were without damage. And there was no coating from luminal surface of the inserter been transferred onto the surface of the IOLs.

Example 4

Mutual Irradiation Graft Copolymerization of Hydrophilic and Lubricious Copolymer Brushes onto Silicone-Based Sheets.

Silicone-based sheets for making contact lenses were used as the base polymer and subjected to the same engrafting of hydrophilic and lubricious copolymer brushes process as the above-described Example 1. Solutions no. 3 and 15 from Table 1 were used. The resultant silicone sheets had shown excellent and durable hydrophilicity and lubricity on their surfaces.

Example 5

Pre-Irradiation Graft Copolymerization of Hydrophilic and Lubricious Polymeric Brushes onto Polypropylene-Based IOL Inserters.

Using the pre-irradiation graft copolymerization as a different approach from Example 1, typical butterfly-type polypropylene (PP)-based IOL inserters were used as the base polymer. A preparation scheme of the PP-based composition containing a hydrophilic and lubricious group, e.g., an amine group or a sulfonic acid group, consists of three steps: (1) Irradiation of an electron beam onto the PP-based inserters to form radicals: the PP-based inserter was irradiated by an electron beam at ambient temperature. The dose was set at 200 kGy. (2) Graft polymerization of a reactive vinyl monomer: the irradiated PP-base IOL inserters was immersed in 20 v/v % glycidyl methacrylate (GMA)/methanol solution at 313K for various time. (3) Introduction of an acidic group (sulfonic acid group) or an amine group (trimethylammonium group) for hydrophilicity and lubricity: the GMA-grafted PP-based inserter was reacted either with a mixture of sodium sulfite (SS)/isopropyl alcohol/water (10/15/75 weight ratio) at 80° C. for 20 hours or with trimethylammonium (TMA) at 80° C. for 20 hours, to obtain sulfonic acid groups or amine groups on the poly-GMA brushes, respectively. The resultant compositions are referred to as SS inserters or TMA inserters.

The SS and TMA inserters were used to deliver IOL lenses. Both SS and TMA inserters can deliver the IOLs without any damages to the IOLs. And there was no coating from luminal surface of the inserter been transferred onto the surface of the IOLs. The TMA inserters were more lubricious than the SS inserters.

In summary, the graft copolymerized PP-based IOL inserter of the present invention is superior to any known heretofore, capable of delivering a foldable IOL with minimum friction force, without damage, into the eye through a smaller incision. The channel through which the IOL passes is highly hydrophilic and lubricious when wet with water or viscoelastic solution.

The engrafted hydrophilic and lubricious copolymer brushes on the base polymer are permanent, do not detach from the base polymer, can be stored in wet stage and can withstand steam sterilization. Thus eliminating the transfer of hydrophilic and lubricious compositions into the eye during the IOL insertion process as well as enabling the design of a preloaded device containing hydrophilic IOL packaged in water or saline. The same system can also be used to design a preloaded device containing hydrophobic IOL packaged in a dry state.

Example 6

Mutual Irradiation Graft Copolymerization of Hydrophilic and Lubricious Copolymer Brushes onto Various Polymers.

Typical polyurethane (PU)-, polyvinyl alcohol (PVC)-, polytetrafluoroethylene (PTFE)-, high density polyethylene (HDPE)-, polyether block amide (PEBAX)- and ethylvinylacetate-based polymeric tubes were used as the base polymer. 2-hydroxyethyl methacrylate (HEMA) was used as the hydrophilic reactive monomer and 2acrylamido-2-methylpropane sulfonic acid (AMPS) was used as the lubricious reactive monomer. The molar ratio of HEMA:AMPS was set at 1:1 and butanol was used as the solvent. The electron-beam irradiation dose was set at 25 kGy. All experimental methods followed Example 1. The resultant hydrophilic and lubricious polymer compositions were subjected to wettability and lubricity tests. In the wettability test, contact angle of each untreated and treated polymer was measured. The contact angles were found to decreased from 10% to 70%. For the lubricity tests, all treated polymers were subjected to finger-rubbing test after been immersed in water for 1 min. The finger-rubbing tests were compared to those of the untreated original polymers. Friction force was felt during rubbing by fingers on each untreated original polymer, whereas for all treated polymers, their surface were slippery. As a result, the mutual irradiation graft copolymerization of hydrophilic and lubricious copolymer brushes had made various polymers hydrophilic and lubricious.

EQUIVALENTS

The invention can be modified in many ways, within the scope of the preceding disclosure. The specific choice of materials for the hydrophilic and lubricious copolymer brushes can be varied, as described above. The graft copolymerization of the hydrophilic and lubricious copolymer brushes can also be applied to the whole or partial portion of the IOL inserter to obtain the thinnest layer of hydrophilic and lubricious polymeric matrix enabling the smallest incision, where the friction between the inner wall of the IOL inserter and the IOL is likely to be the greatest. These and other modifications, which will be apparent to those skilled in the art, should be considered within the spirit and scope of the following claims.

What is claimed is:

1. A method for modifying a hydrophobic base polymer comprising: obtaining a non-irradiated base polymer that is substantially hydrophobic and engrafting thereto a hydrophilic surface, said hydrophilic surface further comprising an engrafted surface matrix of hydrophilic and lubricious copolymers, the engraftment method further comprising the steps of:
- a. contacting the base polymer with a mixed surface modifying solution comprising: an anhydrous alcohol, a hydrophilic reactive monomer and a lubricious reactive monomer; and
- b. initiating radical formation in the base polymer in the mixed surface modifying solution via electron beam irradiation;

thereby engrafting the hydrophilic reactive monomers and the lubricious reactive monomers on to the surface of the base polymer thereby providing a modified base polymer with a thin, durable, and sterilizable hydrophilic and lubricious secondary polymeric matrix.

2. The method of claim 1, wherein the base polymer is a hydrophobic bulk matrix selected from the group consisting of polypropylene, polycarbonate, polyethylene, acryl-butadiene styrene, polyamide, polychlorotrifluoroethylene, polytetrafluoroethylene, polyvinyl chloride, polyvinylidene fluoride, polyvinylchloride, polydimethylsiloxane, polyethylene terephthalate, ethylene tetrafluoroethylene, ethylene chlorotrifluoroethylene, perfluoroalkoxy, styrene, polymethylpentene, polymethylmethacrylate, polystyrene, polyetheretherketone, tetrafluoroethylene, polyurethane, poly(methyl methacrylate), poly (2-hydroxyethyl methacrylate), nylon, polyether block amide and silicone.

3. The method of claim 2, wherein the base polymer is polypropylene or polycarbonate that forms an intraocular lens delivery device having a luminal surface comprising the hydrophilic surface having an engrafted hydrophilic and lubricious polymer matrix.

4. The method of claim 2, wherein the base polymer is silicone that forms a contact lens having a substantially concave surface and a substantially convex surface, and the substantially concave surface and substantially convex surface comprise the engrafted hydrophilic surface having the hydrophilic and lubricious copolymer matrix.

5. The method of claim 1, wherein the hydrophilic reactive monomer is present in the surface modifying copolymeric matrix in an amount of about 10 wt % to about 90 wt % and is selected from the group consisting of: 2-acrylamido-2-methylpropane sulfonic acid, 2-hydroxyethyl methacrylate, N-vinylpyrrolidone, vinylbenzyltrimethyl ammonium salt, diethylaminoethyl methacrylate, dimethylaminoethyl acrylate, dimethylaminoethyl methacrylate, diethylaminoethyl acrylate, diethylaminomethyl methacrylate, tertiary¬butylaminoethyl acrylate, tertiary-butylaminoethyl methacrylate and dimethylaminopropylacrylamide, acrylic acid, methacrylic acid, styrenesulfonic acid and salts thereof, hydroxypropyl acrylate, vinylpyrrolidone, dimethylacrylamide, ethylene glycol monomethacrylate, ethylene glycol monoacrylate, ethylene glycol dimethacrylate, ethylene glycol diacrylate, triethylene glycol diacrylate and triethylene glycol methacrylate.

6. The method of claim 5, wherein the hydrophilic reactive monomer is 2-hydroxyethyl methacrylate.

7. The method of claim 1, wherein the lubricious reactive monomer is present in the surface modifying copolymeric matrix in an amount of about 10 wt % to about 90 wt %, and is selected from the group consisting of: 2-acrylamido-2-methylpropane sulfonic acid, 2-hydroxyethyl methacrylate, N-vinylpyrrolidone, vinylbenzyltrimethyl ammonium salt, diethylaminoethyl methacrylate, dimethylaminoethyl acrylate, dimethylaminoethyl methacrylate, diethylaminoethyl acrylate, diethylaminomethyl methacrylate, tertiary-butylaminoethyl acrylate, tertiary-butylaminoethyl methacrylate and dimethylaminopropylacrylamide, acrylic acid, methacrylic acid, styrenesulfonic acid and salts thereof, hydroxypropyl acrylate, vinylpyrrolidone, dimethylacrylamide, ethylene glycol monomethacrylate, ethylene glycol monoacrylate, ethylene glycol dimethacrylate, ethylene glycol diacrylate, triethylene glycol diacrylate and triethylene glycol methacrylate.

8. The method of claim 7, wherein the lubricious reactive monomer is 2-acrylamido-2-methylpropane sulfonic acid.

9. The method of claim 7, wherein the lubricious reactive monomer is acrylic acid.

10. The method of claim 1, further comprising applying the radiant energy source to the base polymer while the base polymer is immersed in a contained solution of reactive monomers.

11. The method of claim 1, wherein the alcohol is selected from the group consisting of: methanol, ethanol, butanol, and isopropyl alcohol.

12. The method of claim 1, further comprising:
- a. removing the engrafted base polymer from the container;
- b. treating the engrafted base polymer with water and optionally a solvent; and
- c. drying the engrafted base polymer.

13. The method of claim 1, wherein the base polymer is polypropylene, the hydrophilic reactive monomer is 2-hydroxyl methacrylate, the lubricious reactive monomer is 2-acrylamido-2-methylpropane sulfonic acid and the alcohol is butanol.

14. The method of claim 1, wherein the base polymer is polycarbonate, the hydrophilic reactive monomer is 2-hydroxyl methacrylate, the lubricious reactive monomer is 2-acrylamido-2-methylpropane sulfonic acid and the alcohol is butanol.

15. The method of claim 1, wherein the base polymer is silicone, the hydrophilic reactive monomer is 2-hydroxyl methacrylate, the lubricious reactive monomer is 2-acrylamido-2-methylpropane sulfonic acid and the alcohol is butanol.

16. The method of claim 1, wherein the base polymer has a substantially tubular geometry defining a luminal surface comprising the hydrophilic surface having an engrafted hydrophilic and lubricious polymer matrix.

* * * * *